United States Patent
Yuro

(10) Patent No.: US 12,239,728 B2
(45) Date of Patent: Mar. 4, 2025

(54) COSMETIC COMPOSITION FOR A MATTE FOUNDATION

(71) Applicant: L'ORÉAL, Paris (FR)

(72) Inventor: Sarah Kathryn Yuro, Jackson, NJ (US)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 17/960,263

(22) Filed: Oct. 5, 2022

(65) Prior Publication Data

US 2024/0115477 A1  Apr. 11, 2024

(51) Int. Cl.
| | |
|---|---|
| A61K 8/49 | (2006.01) |
| A61K 8/25 | (2006.01) |
| A61K 8/29 | (2006.01) |
| A61K 8/73 | (2006.01) |
| A61K 8/891 | (2006.01) |
| A61Q 1/12 | (2006.01) |
| A61Q 17/00 | (2006.01) |

(52) U.S. Cl.
CPC .............. *A61K 8/4946* (2013.01); *A61K 8/25* (2013.01); *A61K 8/29* (2013.01); *A61K 8/732* (2013.01); *A61K 8/891* (2013.01); *A61Q 1/12* (2013.01); *A61Q 17/00* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 2,676,182 A | 4/1954 | Daudt | |
| 3,627,851 A | 12/1971 | Brady | |
| 3,772,247 A | 11/1973 | Flannigan | |
| 4,935,484 A | 6/1990 | Wolfgruber et al. | |
| 5,082,706 A | 1/1992 | Tangney | |
| 5,110,890 A | 5/1992 | Butler | |
| 5,246,694 A | 9/1993 | Birthwistle | |
| 5,248,739 A | 9/1993 | Schmidt et al. | |
| 5,319,040 A | 6/1994 | Wengrovius | |
| 5,750,723 A | 5/1998 | Eldin et al. | |
| 5,847,156 A | 12/1998 | Eldin et al. | |
| 8,124,710 B2 | 2/2012 | Cook et al. | |
| 8,637,057 B2 | 1/2014 | Patel et al. | |
| 2016/0089312 A1* | 3/2016 | Dique-Mouton | A61K 8/064 424/63 |
| 2017/0304658 A1 | 10/2017 | L'Oreal | |

FOREIGN PATENT DOCUMENTS

| | | |
|---|---|---|
| EP | 0542669 A1 | 5/1993 |
| EP | 0787730 A1 | 8/1997 |
| EP | 0787731 A2 | 8/1997 |
| EP | 3185843 B1 | 8/2021 |
| ES | 2864325 A1 | 10/2021 |
| JP | 2012048258 B2 | 3/2012 |
| WO | 96/08537 A1 | 3/1996 |
| WO | 2016000145 A1 | 1/2016 |
| WO | 2021102873 A1 | 6/2021 |
| WO | 2021119770 A1 | 6/2021 |
| WO | 2022000054 A1 | 1/2022 |

OTHER PUBLICATIONS

French Search Report, and Written Opinion, for corresponding French Application No. 2300105, dated Nov. 23, 2023.

* cited by examiner

*Primary Examiner* — Nicole P Babson
(74) *Attorney, Agent, or Firm* — MEAGHER EMANUEL LAKS GOLDBERG & LIAO, LLP

(57) ABSTRACT

A cosmetic composition for providing a matte foundation may be provided, that includes a mattifying filler, a colorant, a hydrocarbon-based oil, a hydrocarbon-based emulsifier, water, and UV filter system consisting of an organic hydrophobic UV filter, an organic water-soluble UV filter, and an inorganic UV filter. The mattifying filler may consist of a silica aerogel and optionally a modified starch, amorphous silica, a clay, and/or a silicone elastomer. The organic hydrophobic UV filter may consist of octyl salicylate, and the cosmetic composition may be free of other organic hydrophobic ultraviolet filters. The organic water-soluble ultraviolet filter may consist of 2-phenylbenzimidazole-5-sulfonic acid (PBSA), and the cosmetic composition may be free of other organic water-soluble ultraviolet filters. The inorganic UV filter may consist of UV-grade titanium dioxide, and the cosmetic composition may be free of other inorganic ultraviolet filters.

5 Claims, No Drawings

COSMETIC COMPOSITION FOR A MATTE FOUNDATION

TECHNICAL FIELD

The present application is drawn to cosmetic compositions for use as matte foundations, and specifically foundations having higher sun protection factor (SPF) values, shine control, and large depth and clarity of shade.

BACKGROUND

Conventional matte foundations that can be used with a diverse range of skin pigmentation either do not contain ultraviolet (UV) filters or contain only relatively low levels of UV filters (e.g., sufficient for an SPF of 20 or below). This is because conventional UV filter systems compromise the characteristics required for matte foundations. Specifically, using a high level of organic UV filters (to achieve a higher SPF) system, which would allow for the formula to achieve deep shades, but would have too high of a refractive index to provide shine control and a matte finish. Conversely, using a high level of inorganic UV filters (or "physical" sun filters) would make it easier to provide shine control and a matte finish, but compromise on the depth and clarity of shade.

Thus, what is needed is a composition that can be used as a foundation that can provide the characteristics required—a high degree of shine control, a matte finish, and a large depth and clarity of shade.

BRIEF SUMMARY

To provide the required characteristics, while providing a relatively high SPF (e.g., SPF>20), a cosmetic composition may be provided. The cosmetic composition may also provide an optical blurring effect to minimize the appearance of pores, as well as shine control and skincare benefits over time to improve dryness, blemishes, and signs of aging.

The cosmetic composition for providing a matte foundation may include a mattifying filler, a colorant, a hydrocarbon-based oil, a hydrocarbon-based emulsifier, water, and UV filter system consisting of an organic hydrophobic UV filter, an organic water-soluble UV filter, and an inorganic UV filter. The mattifying filler may consist of a silica aerogel and optionally a modified starch, amorphous silica, a clay, and/or a silicone elastomer. The organic hydrophobic UV filter may consist of octyl salicylate, and the cosmetic composition may be free of other organic hydrophobic ultraviolet filters. The organic water-soluble ultraviolet filter may consist of 2-phenylbenzimidazole-5-sulfonic acid (PBSA), and the cosmetic composition may be free of other organic water-soluble ultraviolet filters. The inorganic UV filter may consist of UV-grade titanium dioxide, and the cosmetic composition may be free of other inorganic ultraviolet filters.

In some embodiments, the composition may be a water-in-oil emulsion. In some embodiments, the inorganic ultraviolet filter may be present in an amount less than 5% by weight of the composition. In some embodiments, the inorganic ultraviolet filter may be present in an amount less than 3% by weight of the composition. In some embodiments, the mattifying filler may be present in an amount less than 10% by weight of the composition. In some embodiments, the composition may include a polyol. In some embodiments, the composition may include a non-volatile silicone oil. In some embodiments, the composition may include a vitamin. In some embodiments, the amount of the hydrocarbon-based oil plus the amount of the non-volatile silicone oil may be less than 30% by weight of the composition. In preferred embodiments, the cosmetic composition may be free of volatile silicone oils. In some embodiments, the hydrocarbon-based oil may be present in an amount less than 10% by weight of the composition. In some embodiments, the colorant may be present in an amount of less than 30% by weight of the composition. In some embodiments, the colorant may consist of one or more pigments, each pigment is preferably coated. In some embodiments, the one or more pigments comprises pigment-grade titanium dioxide. In some embodiments, the composition may include a preservative, a silicone resin, a thickening agent, a pH adjusting or buffering agent, an electrolyte, a flavonoid, a synthetic peptide, and/or an amino acid or amino acid derivative.

In some embodiments, the composition may include the mattifying filler, colorant, hydrocarbon-based oil, hydrocarbon-based emulsifier, water, and UV filter system, may optionally include a polyol, a non-volatile silicone oil, a vitamin, a preservative, a silicone resin, a thickening agent, a pH adjusting or buffering agent, an electrolyte, a flavonoid, a synthetic peptide, and/or an amino acid or amino acid derivative, may be optionally free of a volatile silicone oil, and may be substantially free of all other materials.

A method may be provided for applying cosmetics to a face. The method may include applying the cosmetic composition as disclosed herein to the face during a first period of time, and then removing the cosmetic composition from the face during a second period of time after the first period of time. In some embodiments, the method may include applying a second composition over the cosmetic composition after the first period of time and before the second period of time.

DETAILED DESCRIPTION

In the following description of the invention and the claims appended hereto, it is to be understood that the terms used have their ordinary and accustomed meanings in the art, unless otherwise specified. All concentrations are by weight percent on an active basis unless otherwise indicated.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

The term "matte" as used herein refers to a non-shiny, non-glossy finish. As used herein, the term matte may be used to describe the finish provided by a composition to a substrate, such as rendering oily or combination skin matte, as well as to describe the finish of a composition on a substrate, such a matte film of lipstick on lips. In some cases, the degree of matteness of a composition can be measured using a gonioreflectometer to measure the reflection, R, of a composition, wherein R is the ratio of the specular reflection to the diffuse reflection. The lower the value of R, the higher the mattifying effect. Preferably, R is less than 1.6. In some cases, the degree of matteness of a composition on a substrate is also measured using a gloss meter to measure the gloss of a film in terms of % reflectance, where lower reflectance has a higher degree of matteness. Preferably, reflectance may be 5% or less.

The term "substantially free" as used herein refers to a particular material that may be present at less than 1 wt % based on the total weight of the composition, and without materially affecting the basic and novel characteristics of the claimed invention. In some cases, the composition may contain less than 0.5 wt. %, less than 0.1 wt. %, less than 0.05 wt. %, or less than 0.01 wt. % of the specified material or be completely free of the specified material.

A cosmetic composition that can create a matte foundation may be provided.

Mattifying Filler

The cosmetic composition may include a mattifying filler. The mattifying filler may consist of a silica aerogel, and optionally a modified starch, amorphous silica, a clay, and/or a silicone elastomer.

In some embodiments, the mattifying filler present may be present in the composition at no more than 15%, 12%, 10%, 9%, 8%, or 7% by weight of the composition. In some embodiments, the total amount of mattifying filler present in the composition is preferably no more than 7% by weight of the composition.

Silica Aerogel.

The amount of silica aerogel present in the compositions will typically be at least 0.5%, or at least 0.6%, or at least 0.7% by weight of the composition. It will typically be at most 0.7%, or at most 0.8%, or at most 0.9% by weight of the composition.

Silica aerogels are porous materials obtained by replacing (by drying) the liquid component of a silica gel with air. They are generally synthesized via a sol-gel process in liquid medium and then dried, usually by extraction of a supercritical fluid, the one most commonly used being supercritical $CO_2$.

The hydrophobic silica aerogel particles used in the present invention have a specific surface area per unit of mass (SM) ranging from 500 to 1500 $m^2/g$, preferably from 600 to 1200 $m^2/g$ and better still from 600 to 800 $m^2/g$, and a size expressed as the mean volume diameter (D[0.5]), ranging from 1 to 30 μm, preferably from 5 to 25 μm, better still from 5 to 20 μm and even better still from 5 to 15 μm. The specific surface area per unit of mass may be determined via the BET (Brunauer-Emmett-Teller) nitrogen absorption method described in the Journal of the American Chemical Society, vol. 60, page 309, February 1938 and corresponding to the international standard ISO 5794/1 (appendix D). The BET specific surface area corresponds to the total specific surface area of the particles under consideration.

The size of the silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter.

In some embodiments, the hydrophobic silica aerogel particles may have a specific surface area per unit of mass (SM) ranging from 600 to 800 $m^2/g$ and a size expressed as the mean volume diameter (D[0.5]) ranging from 5 to 20 μm and better still from 5 to 15 μm.

In some embodiments, the hydrophobic silica aerogel particles may have a specific surface area per unit of volume Sv ranging from 5 to 60 $m^2/cm^3$, preferably from 10 to 50 $m^2/cm^3$ and better still from 15 to 40 $m^2/cm^3$.

In some embodiments, the hydrophobic silica aerogel particles may have an oil-absorbing capacity, measured at the wet point, ranging from 5 to 18 mL/g, preferably from 6 to 15 mL/g and better still from 8 to 12 mL/g. The oil-absorbing capacity measured at the wet point, noted Wp, corresponds to the amount of water that needs to be added to 100 g of particle in order to obtain a homogeneous paste. It is measured according to the wet point method or the method for determining the oil uptake of a powder described in standard NFT 30-022. It corresponds to the amount of oil adsorbed onto the available surface of the powder and/or absorbed by the powder by measuring the wet point.

In some embodiments, the silica aerogels may be hydrophobic silica aerogels, and may preferably be silylated silica (INCI name: silica silylate).

As used herein, the term "hydrophobic silica" refers to any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups. In some embodiments, the silica aerogel may be hydrophobic silica aerogels particles surface-modified with trimethylsilyl groups. Non-limiting examples of silica aerogels include the aerogel sold under the name VM-2260 (INCI name: Silica silylate), by the company Dow Corning, the particles of which have a mean size of about 1000 μm and a specific surface area per unit of mass ranging from 600 to 800 $m^2/g$; aerogels sold by the company Cabot under the references Aerogel TLD 201, Aerogel OGD 201 and AerogelTLD 203, Enova Aerogel MT 1 100 and Enova Aerogel MT 1200. In some embodiments, the aerogel may be an aerogel sold under the name VM-2270 (INCI name: Silica silylate), by the company Dow Corning, the particles of which have a mean size ranging from 5-15 μm and a specific surface area per unit of mass ranging from 600 to 800 $m^2/g$. It has an oil absorption capability of 1090 mL/100 g based on isononyl isononanoate.

Modified Starch.

The amount of modified starch present in the compositions, if included, will typically be at least 0.5%, or at least 0.75%, or at least 1% by weight of the composition. It will typically be at most 1%, or at most 1.5%, or at most 2% by weight of the composition.

Modified starch is starch which has been modified by methods known to those skilled in the art, such as, for example, esterification, etherification, oxidation, acid hydrolysis, crosslinking, or enzymatic conversion. The modified starch may be a hydrophobically modified starch.

Non-limiting examples of modified starch include octenyl succinate aluminum starch, octenyl succinate sodium starch, octenyl succinate calcium starch, diamidon phosphate, hydroxyethyl phosphate starch, hydroxypropyl starch phosphate, sodium carboxymethyl starch, and sodium starch glycolate.

In some embodiments, the modified starch may be an octenylsuccinate of starch, in particular of aluminum, the starch being corn, wheat or rice. Mention may in particular be made of the product offered by AKZO NOBEL under the name DRY FLO PLUS. We can also mention rice starch such as the product D.S.A.7 offered by the company Agrana Starch.

Amorphous Silica.

The amount of modified starch present in the compositions, if included, will typically be at least 1%, or at least 2%, or at least 3% by weight of the composition. It will typically be at most 5%, or at most 7%, or at most 10% by weight of the composition.

The compositions of the present invention may be spherical amorphous silica. By "spherical" amorphous silica, it is meant particulate silica which is substantially spherical. In some embodiments, the spherical amorphous silica may be coated with a hydrophobic treatment agent. In some embodiments, the spherical silica is a "native" silica, that is to say without hydrophobic surface treatment, and can have a chemical purity of at least 90%, such as at least 95% or at least 98% relative to silica. In some embodiments, the average size of these spherical amorphous silica particles is less than 15.0 microns and is more particularly in a range of 3 to 10 microns.

The spherical amorphous silica particles useful according to the invention are colorless or white solid particles of any shape, which are in an insoluble form and dispersed in the medium of the composition.

Non-limiting examples of amorphous silica include porous silica microspheres sold as SilicaBeads SB-700 by Myoshi Company (average size 4.6 microns and oil absorption capacity Wp: 133 mL/100 g); Sunsphere® H51 (average size 5.1 microns and oil absorption capacity Wp: 133 mL/100 g), Sunsphere® H33 (average size 2.9 microns and oil absorption capacity Wp: 370 mL/100 g) by Asahi Glass Company.

Clay.

The amount of clay present in the compositions, if included, will typically be relatively low, and will typically be at most 0.01% or at most 0.1% by weight of the composition. Such clays, if utilized, may be either modified clays or natural clays, and are preferably non-swelling clays. In some embodiments, the clay may be, e.g., kaolin.

Silicone Elastomer.

The amount of silicone elastomer present in the compositions, if included, will typically be at least 0.5%, or at least 0.75%, or at least 1% by weight of the composition. It will typically be at most 1%, or at most 1.5%, or at most 2% by weight of the composition.

The silicone elastomer should be a mattifying silicone polymer. The silicone elastomer may be a non-emulsifying silicon elastomer. The term "non-emulsifying" as used herein refers to organopolysiloxane elastomers that do not contain hydrophilic chains, in particular polyoxyalkylene (especially polyoxyethylene or polyoxypropylene) or polyglyceryl units. Thus, according to some embodiments, the composition mays comprises a silicone elastomer that is free of polyoxyalkylene units and polyglyceryl units.

Non-limiting of non-emulsifying elastomers are described in U.S. Pat. No. 8,637,057, the disclosure of which is hereby incorporated by reference in its entirety, as well as those sold under the names KSG-6, KSG-15, KSG-16, KSG-18, KSG-41, KSG-42, KSG-43 and KSG-44 by the company Shin-Etsu, DC 9040, DC 9041, DC 9509, DC 9505 and DC 9506, by the company Dow Corning, and SFE 839 by the company General Electric.

The silicone elastomers may be in the form of a gel or a powder.

In some embodiments, the silicone elastomer may be conveyed in the form of a gel formed from an elastomeric organopolysiloxane included in at least one hydrocarbon-based oil and/or one silicone oil. In these gels, the organopolysiloxane particles are often non-spherical particles. Not limiting examples of silicone elastomers useful in this invention are dimethicone crosspolymer gels (blends of dimethicone crosspolymers in solvents) having viscosity values from about 150 and to about 700 mm²/s, from about 200 to about 650 mm²/s and from about 300 to about 600 mm²/s, including all ranges and subranges therebetween.

Non-limiting examples of silicone elastomeric gels include DC EL-8040 ID (INCI name: Isododecane (and) Dimethicone Crosspolymer) and DC EL-9140 DM (INCI name: Dimethicone (and) DimethiconeCrosspolymer), supplied by Dow Corning.

Although not wishing to be bound by any particular theory, it is believed that the silicone elastomer thickens the composition, adds a cushiony (spongy) effect and/or improves the application properties of the cosmetic composition. Also, it provides a very soft feel and mattifying effect after application.

UV Filter System

The cosmetic composition may include a UV filter system, In some embodiments, UV filter system consists of an organic hydrophobic UV filter, an organic water-soluble UV filter, and an inorganic UV filter. Such UV filters are active in the UVA and/or/UVB wavelengths.

Organic Hydrophobic UV Filter.

The organic hydrophobic UV filter may consist of octyl salicylate (also referred to as ethylhexyl salicylate). The cosmetic composition may be free of other organic hydrophobic ultraviolet filters. The organic hydrophobic UV filter will typically be present in an amount of no more than 5% by weight of the composition. The organic hydrophobic UV filter will typically be present in an amount of 3-5% by weight of the composition.

Organic Water-Soluble UV Filter.

The organic water-soluble UV filter may consist of 2-phenylbenzimidazole-5-sulfonic acid (PB SA). The cosmetic composition may be free of other organic water-soluble ultraviolet filters. The organic water-soluble UV filter will typically be present in an amount of no more than 4% by weight of the composition. The organic hydrophobic UV filter will typically be present in an amount of 2-4% by weight of the composition. A ratio of the amount of organic hydrophobic UV filter to the amount of water-soluble UV filter will typically be 1.25:1 to 1.75:1.

Inorganic UV Filter.

The inorganic UV filter may consist of UV-grade titanium dioxide, and the cosmetic composition may be free of other inorganic ultraviolet filters. "UV-grade" titanium dioxide generally has a relatively small particle size—typically having mean particle sizes of 250 nm or smaller, including 200 nm or smaller, and/or 150 nm or smaller. In some cases, the average particle size is around 130 nm.

The inorganic UV filter will typically be present in an amount less than 5% by weight of the composition. In some embodiments, the inorganic UV filter may be present in an amount less than 3% by weight of the composition. In some embodiments, the inorganic UV filter may be present in an amount less than the amount of either the organic hydrophobic UV filter or the organic water-soluble UV filter.

In some embodiments, the inorganic ultraviolet filter may be present in an amount less than 5% by weight of the composition. In some embodiments, the inorganic ultraviolet filter may be present in an amount less than 3% by weight of the composition.

Colorant

The cosmetic composition may include a colorant. In some embodiments, the colorant may be present in an amount of less than 30% by weight of the composition. In some embodiments, the colorant may be present in an amount of less than 20% by weight of the composition. In some embodiments, the colorant may be present in an amount of at least 10% by weight of the composition.

The colorant(s) may be selected from organic and/or inorganic colorants, in particular such as pigments or nacres conventionally used in cosmetic compositions, liposoluble or water-soluble coloring agents, materials with a specific optical effect, and mixtures thereof.

Pigments.

The colorant may include, or consist of, one or more pigments. Each pigment is preferably coated. In some embodiments, the one or more pigments comprises pigment-grade titanium dioxide. "Pigment-grade" titanium dioxide generally has a larger particle size than UV grade titanium dioxide—typically having mean particle sizes of 400 nm or larger, including 500 nm or larger, and/or 600 nm or larger.

The term "pigments" should be understood to mean white or colored, inorganic or organic particles which are insoluble in an aqueous solution and are intended for coloring and/or opacifying the resulting film.

The pigments may be present in a proportion of from 0.1% to 30% by weight, such as from 1% to 30% by weight, or from 5% to 20% by weight, relative to the total weight of the cosmetic composition.

As inorganic pigments that can be used, mention may be made of titanium dioxide, zirconium oxide or cerium oxide, and also zinc oxide, iron oxide or chromium oxide, ferric blue, manganese violet, ultramarine blue and chromium hydrate.

The pigment may also be a pigment having a structure which may be, for example, of sericite/brown iron oxide/titanium dioxide/silica type. Such a pigment is sold, for example, under the reference Coverleaf NS or JS by the company Chemicals and Catalysts and has a contrast ratio of around 30.

The colorant may also comprise a pigment having a structure which may, for example, be of the type of silica microspheres containing iron oxide. An example of a pigment having this structure is sold by the company Miyoshi under the reference PC Ball PC-LL-100 P, this pigment being composed of silica microspheres containing yellow iron oxide.

Among the organic pigments that can be used, mention may be made of carbon black, D & C pigments, lakes based on cochineal carmine, on barium, strontium, calcium or aluminum, or else the diketopyrrolopyrroles (DPP) described in documents EP-A-542 669, EP-A-787 730, EP-A-787 731 and WO-A-96/08537.

In some embodiments, the coating may include alumina, silica, aluminum hydroxide, or pigment-grade titanium dioxide, and a hydrocarbon-based emulsifier as disclosed herein. In some embodiments, the coating may be present in a total amount of less than 1% by weight of the composition.

When iron oxides are present, such iron oxides (i.e., excluding coatings) are present in a total amount of no more than 5% by weight of the composition. In some embodiments, such iron oxides (excluding coatings) are present in a total amount of no more than 3% by weight of the composition. In some embodiments, such iron oxides (excluding coatings) are present in a total amount of no more than 2% by weight of the composition. In some embodiments, such iron oxides (excluding coatings) are present in a total amount of 1-1.5% by weight of the composition.

When pigment-grade titanium dioxide is present, such pigment-grade titanium dioxide (i.e., excluding coatings) is present in a total amount of no more than 25% by weight of the composition. In some embodiments, such pigment-grade titanium dioxide (excluding coatings) are present in a total amount of no more than 20% by weight of the composition. In some embodiments, such pigment-grade titanium dioxide (excluding coatings) is present in a total amount of 10-20% by weight of the composition. In some embodiments, such pigment-grade titanium dioxide (excluding coatings) is present in a total amount of 15-20% by weight of the composition.

Nacres.

The colorant may also include one or more nacres. The term "nacres" should be understood to mean iridescent or noniridescent colored particles of any shape, which are in particular produced by certain molluscs in their shell or else are synthesized, and which exhibit a color effect by optical interference.

The nacres may be selected from pearlescent pigments. Such pigments may include natural or synthetic mica (fluorphlogopite). Non-limiting examples of pearlescent pigments invention include white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. This may also involve mica particles at the surface of which are superposed at least two successive layers of metal oxides and/or of organic colorants. If pearlescent pigments are present, they are typically present in a total amount of no more than 5% by weight of the composition. In some embodiments, pearlescent pigments are present in a total amount of no more than 3% by weight of the composition. In some embodiments, pearlescent pigments are present in a total amount of no more than 2% by weight of the composition.

Among the nacres available on the market, mention may be made of the nacres Timica, Flamenco and Duochrome (based on mica) sold by the company Engelhard, the Timiron nacres sold by the company Merck, the Prestige mica-based nacres sold by the company Eckart and the synthetic-mica-based Sunshine nacres sold by the company Sun Chemical.

The nacres may more particularly possess a yellow, pink, red, bronze, orange, brown, gold and/or copper color or glint.

By way of illustration of nacres which can be used in the context of the present disclosure, mention may in particular be made of the golden nacres sold in particular by the hcompany Engelhard under the name Brillant gold 212G (Timica), Gold 222C (Cloisonne), Sparkle gold (Timica), Gold 4504 (Chromalite) and Monarch gold 233X (Cloisonne); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown-hued nacres sold in particular by the company Engelhard under the name Nu-antique copper 340XB (Cloisonne) and Brown CL4509 (Chromalite); the copper-glint nacres sold in particular by the company Engelhard under the name Copper 340A (Timica); the red-glint nacres sold in particular by the company Merck under the name Sienna fine (17386) (Colorona); the yellow-glint nacres sold in particular by the company Engelhard under the name Yellow (4502) (Chromalite); the gold-glint red-hued nacres sold in particular by the company Engelhard under the name Sunstone G012 (Gemtone); the pink nacres sold in particular by the company Engelhard under the name Tan opale G005 (Gemtone); the gold-glint black nacres sold in particular by the company Engelhard under the name Nu antique bronze 240 AB (Timica), the blue nacres sold in particular by the company Merck under the name Matte blue (17433) (Microna), the silver-glint white nacres sold in particular by the company Merck under the name Xirona Silver and the green-gold and pinkish orangish nacres sold in particular by the company Merck under the name Indian summer (Xirona), and mixtures thereof.

Dyes.

The colorant may also include water-soluble or liposoluble dyes. The liposoluble dyes are, for example, Sudan red, DC Red 17, DC Green 6, β-carotene, soya oil, Sudan brown, DC Yellow 11, DC Violet 2, DC orange 5 and quinoline yellow. The water-soluble dyes are, for example, beetroot juice and caramel.

Material with a Special Optical Effect.

The colorant may also include at least one material with a specific optical effect. This effect is different than a simple, conventional hue effect, i.e., a unified and stabilized effect of the kind produced by conventional colorants, such as, for example, monochromatic pigments. For the purpose of the present disclosure, the term "stabilized" signifies absence of an effect of variability of color with the angle of observation or else in response to a temperature change. For example, this material may be selected from particles having a metallic glint, goniochromatic coloring agents, diffracting pigments, thermochromatic agents, optical brighteners, and also fibers, in particular of interference type. Of course, these various materials may be combined so as to provide the simultaneous manifestation of two effects, or even a new effect.

The metallic-glint particles that can be used in the present disclosure are in particular selected from: (i) particles of at least one metal and/or of at least one metal derivative; (ii) particles comprising a single-substance or multi-substance, organic or inorganic substrate, at least partially coated with at least one metal-glint layer comprising at least one metal and/or at least one metal derivative, and (iii) mixtures of such particles. The term "metal derivatives" denotes compounds derived from metals, in particular oxides, fluorides, chlorides and sulfides.

Non-limiting examples of metals that may be present in such particles include Ag, Au, Cu, Al, Ni, Sn, Mg, Cr, Mo, Ti, Zr, Pt, Va, Rb, W, Zn, Ge, Te, Se and mixtures or alloys thereof, such as Ag, Au, Cu, Al, Zn, Ni, Mo, Cr and mixtures or alloys thereof (for example, bronzes and brasses).

By way of illustration of these particles, mention may be made of aluminum particles, such as those sold under the names STARBRITE 1200 EAC® by the company Siberline and METALURE® by the company Eckart. Mention may also be made of metal powders of copper or of alloy mixtures, such as the references 2844 sold by the company Radium Bronze, metal pigments, such as aluminum or bronze, for instance those sold under the name Rotosafe 700 by the company Eckart, the silica-coated aluminum particles sold under the name Visionaire Bright Silver from the company Eckart, and the metal alloy particles such as silica-coated bronze (copper and zinc alloy) sold under the name Visionaire Bright Natural Gold from the company Eckart. The particles in question may also be particles comprising a glass substrate, such as those sold by the company Nippon Sheet Glass under the name Microglass Metashine.

The goniochromatic coloring agent may be selected, for example, from multilayer interference structures and liquid-crystal coloring agents.

Examples of symmetrical multilayer interference structures that may be used in compositions prepared in accordance with the present disclosure are, for example, the following structures: Al/SiO2/Al/SiO2/Al, pigments having this structure being sold by the company Dupont de Nemours; Cr/MgF2/Al/MgF2/Cr, pigments having this structure being sold under the name Chromaflair by the company Flex; MoS2/SiO2/Al/SiO2/MoS2; Fe2O3/SiO2/Al/SiO2/Fe2O3 and Fe2O3/SiO2/Fe2O3/SiO2/Fe2O3, pigments having these structures being sold under the name Sicopearl by the company BASF; MoS2/SiO2/mica-oxide/SiO2/MoS2; Fe2O3/SiO2/mica-oxide/SiO2/Fe2O3; TiO2/SiO2/TiO2 and TiO2/Al2O3/TiO2; SnO/TiO2/SiO2/TiO2/SnO; Fe2O3/SiO2/Fe2O3; SnO/mica/TiO2/SiO2/TiO2/mica/SnO, pigments having these structures being sold under the name Xirona by the company Merck (Darmstadt). By way of example, these pigments may be the pigments of silica/titanium oxide/tin oxide structure sold under the name Xirona Magic by the company Merck, the pigments of silica/brown iron oxide structure sold under the name Xirona Indian Summer by the company Merck and the pigments of silica/titanium oxide/mica/tin oxide structure sold under the name Xirona Carribean Blue sold by the company Merck. Mention may also be made of the Infinite Colors pigments from the company Shiseido. Depending on the thickness and the nature of the various layers, various effects are obtained. Thus, with the Fe2O3/SiO2/Al/SiO2/Fe2O3 structure, the color changes from green-golden to red-gray for SiO2 layers of 320 to 350 nm; from red to golden for SiO2 layers of 380 to 400 nm; from violet to green for SiO2 layers of 410 to 420 nm; from copper to red for SiO2 layers of 430 to 440 nm.

By way of example of pigments with a polymeric multilayer structure, mention may be made of those sold by the company 3M under the name Color Glitter.

Examples of liquid-crystal goniochromatic particles that may be used include those sold by the company Chenix, and also the product sold under the name HELICONE® HC by the company Wacker.

Hydrocarbon-Based Oil.

The cosmetic composition may include a hydrocarbon-based oil. In some embodiments, the hydrocarbon-based oil may be present in a total amount no more than 15% by weight of the composition. In some embodiments, the hydrocarbon-based oil may be present in a total amount no more than 12% by weight of the composition. In some embodiments, the hydrocarbon-based oil may be present in a total amount between 5% and 15% by weight. In some embodiments, the hydrocarbon-based oil may be present in a total amount between 7% and 12% by weight.

The term "oil" means any fatty substance which is in liquid form at room temperature (20-25° C.) and at atmospheric pressure (760 mmHg).

The term "hydrocarbon-based oil" or "hydrocarbon oil" refers to oil mainly containing hydrogen and carbon atoms and possibly oxygen, nitrogen, sulfur and/or phosphorus atoms. In some embodiments, the hydrocarbon-based oil may be linear or branched. In some embodiments, the hydrocarbon-based oil is a hydrocarbon. Representative examples of hydrocarbon-based oils include oils containing from 8 to 16 carbon atoms, and especially branched C8-C16 alkanes (also known as isoparaffins), for instance isododecane (also known as 2,2,4,4,6-pentamethylheptane), and isohexadecane.

In some embodiments, the hydrocarbon-based oil may be apolar (therefore, formed only of carbon and hydrogen atoms).

In some embodiments, the hydrocarbon-based oil may contain from 12 to 18 carbon atoms.

In some embodiments, the hydrocarbon-based oil may include hydrocarbon-based oils of vegetable origin, such as triglycerides made up of fatty acid esters of glycerol, whose fatty acids may have chain lengths that vary from C4 to C24, these chains possibly being linear or branched and saturated or unsaturated; these oils are especially triglycerides of heptanoic or octanoic acid or, alternatively, wheat germ oil, sunflower oil, grapeseed oil, sesame seed oil, corn oil, apricot kernel oil, castor oil, shea, avocado oil, olive oil, soybean oil, sweet almond oil, palm oil, rapeseed oil, cottonseed oil, hazelnut oil, macadamia oil, jojoba oil, alfalfa oil, oil poppy oil, pumpkin oil, courgette oil, blackcurrant oil, evening primrose oil, millet oil, barley oil, *quinoa* oil, rye oil, safflower oil, candlenut oil, passionflower oil, and musk rose; shea butter; or caprylic/capric acid triglycerides, for example those sold by the company Stearineries Dubois or those sold under the names Miglyol 810®, 812® and 818® by the company Dynamit Nobel, In some embodiments, the hydrocarbon-based oil may include synthetic ethers having from 10 to 40 carbon atoms.

In some embodiments, the hydrocarbon-based oil may include linear or branched hydrocarbons of mineral or synthetic origin, such as petrolatum, polydecenes, hydrogenated polyisobutene such as Parleam®, squalane and liquid paraffins and mixtures thereof.

In some embodiments, the hydrocarbon-based oil may include synthetic esters, such as oils of formula $R^1COOR^2$, in which $R^1$ represents a linear or branched fatty acid residue containing from 1 to 40 carbon atoms and $R^2$ represents a hydrocarbon-based chain, in particular branched, containing from 1 to 40 carbon atoms, provided that $R^1+R^2 \geq 10$, for example purcellin oil (cetostearyl octanoate), isopropyl myristate, isopropyl palmitate, $C^{12}$ to $C^{15}$ alkyl benzoates, hexyl laurate, diisopropyl adipate, isononyl isononanoate, 2-ethylhexyl, isostearyl isostearate, 2-hexyldecyl laurate, 2-octyldecyl palmitate, 2-octyldodecyl myristate, alkyl or polyalkyl heptanoates, octanoates, decanoates or ricinoleates, such as propylene glycol dioctanoate; hydroxylated esters, such as isostearyl lactate, diisostearyl maleate, and 2-octyldodecyl lactate; and polyol esters and pentaerythritol esters. Other synthetic esters may include, e.g., butyloctyl salicylate.

In some embodiments, the hydrocarbon-based oil may include fatty alcohols that are liquid at room temperature, with a branched and/or unsaturated carbon-based chain containing from 12 to 26 carbon atoms, for example, octyldodecanol, isostearyl alcohol, oleyl alcohol, 2-hexyldecanol, 2-butyl octanol and 2-undecylpentadecanol.

In some embodiments, the hydrocarbon-based oil may include a $C_{12}$-$C_{22}$ fatty acid chain, such as those selected from stearic acid, palmitic acid, oleic acid, linoleic acid, linolenic acid, etc., and mixtures thereof. Preferably these fatty acids chains are hydrogenated.

The hydrocarbon-based oil may be volatile or non-volatile.

The term "volatile" oil relates to an oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile" oil relates to oil which remains on the skin or the keratin fiber, at room temperature and atmospheric pressure, for at least several hours and which in particular has a vapor pressure of less than $10^{-3}$ mmHg (0.13 Pa).

In some embodiments, the composition may include no more than 10% by weight of C8-C16 alkanes and no more than 5% by weight of synthetic esters.

Hydrocarbon-Based Emulsifier.

The composition may include one or more hydrocarbon-based emulsifiers. In some embodiments, the composition may include two or more hydrocarbon-based emulsifiers. In some embodiments, the composition may include three or more hydrocarbon-based emulsifiers. In some embodiments, the composition may include four or more hydrocarbon-based emulsifiers.

The hydrocarbon-based emulsifiers are typically present in a total amount no more than 3% by weight of the composition. In some embodiments, the hydrocarbon-based emulsifiers may be present in a total amount no more than 2.5% by weight of the composition. In some embodiments, the hydrocarbon-based emulsifiers may be present in a total amount no more than 2% by weight of the composition. The hydrocarbon-based emulsifiers are typically present in a total amount no less than 1% by weight of the composition. In some embodiments, the hydrocarbon-based emulsifiers may be present in an amount of 1.5% to 2.5% by weight of the composition. In some embodiments, the hydrocarbon-based emulsifiers may be present in an amount of 1% to 2% by weight of the composition.

The hydrocarbon-based emulsifier may include oxyethylenated and/or oxypropylenated ethers (which may comprise from 20 to 1000 oxyethylene and/or oxypropylene groups) of fatty alcohols (especially of $C_8$-$C_{24}$ and preferably $C_{12}$-$C_{18}$ alcohol), such as oxyethylenated stearyl alcohol ether containing 20 oxyethylene groups (CTFA name Steareth-20) such as Brij 78 sold by the company Uniqema, oxyethylenated cetearyl alcohol ether containing 30 oxyethylene groups (CTFA name Ceteareth-30) and the oxyethylenated ether of the mixture of $C_{12}$-$C_{15}$ fatty alcohols comprising 7 oxyethylene groups (CTFA name C12-15 Pareth-7) sold under the name Neodol 25-7® by Shell Chemicals. If oxyethylenated and/or oxypropylenated ethers are present, such are typically present in a total amount no more than 0.01%, 0.1%, or 0.5% by weight of the composition.

The hydrocarbon-based emulsifier may include an amino acid surfactant. Non-limiting examples of amino acid surfactants are salts of alanine, arginine, aspartic acid, glutamic acid, glycine, isoleucine, leucine, lysine, phenylalanine, serine, tyrosine, valine, sarcosine, and any mixture thereof, and specifically, dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, cocoyl methyl β-alaninate, lauroyl β-alaninate, lauroyl methyl β-alaninate, myristoyl β-alaninate, potassium lauroyl methyl β-alaninate, sodium cocoyl alaninate, sodium cocoyl methyl β-alaninate and sodium myristoyl methyl β-alaninate palmitoyl glycinate, sodium lauroyl glycinate, sodium cocoyl glycinate, sodium myristoyl glycinate, potassium lauroyl glycinate, potassium cocoyl glycinate, potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate ammonium lauroyl sarcosinate, sodium lauroyl aspartate, sodium myristoyl aspartate, sodium cocoyl aspartate, sodium caproyl aspartate, disodium lauroyl aspartate, disodium myristoyl aspartate, disodium cocoyl aspartate, disodium caproyl aspartate, potassium lauroyl aspartate, potassium myristoyl aspartate, potassium cocoyl aspartate, potassium caproyl aspartate, dipotassium lauroyl aspartate, dipotassium myristoyl aspartate, dipotassium cocoyl aspartate, dipotassium caproyl aspartate, and mixtures thereof. If amino acid surfactants are present, such are typically present in a total amount no more than 0.75%, 1%, or 1.5% by weight of the composition.

The hydrocarbon-based emulsifier may include a polyol alkyl ester. Non-limiting examples of polyol alkyl esters include glycerol and/or sorbitan esters, for example the polyglyceryl-3 diisostearate sold under the name Lameform TGI by the company Cognis, polyglyceryl-4 isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof. If polyol alkyl ester are present, such are typically present in a total amount no more than 1%, 1.5%, or 2% by weight of the composition.

Water.

The cosmetic composition may include water. Water will typically be present in an amount no more than 30% by weight of the composition. In some embodiments, water may be present in an amount no more than 25% by weight of the composition. In some embodiments, water may be present in an amount no more than 20% by weight of the composition. In some embodiments, water may be present in an amount no less than 10% by weight of the composition. In some embodiments, water may be present in an amount of 15%-25% by weight of the composition.

Other Components.

The cosmetic composition may include one or more other components, including a polyol, a non-volatile silicone oil, a vitamin, a preservative, a silicone resin, a thickening agent, a pH adjusting or buffering agent, an electrolyte, a flavonoid, a synthetic peptide, and/or an amino acid or amino acid derivative.

Polyol.

In some embodiments, the composition may include a polyol. In some embodiments, the polyol may be a hydrocarbon-based polyol. In some embodiments, the polyol may be present in a total amount no more than 15% by weight of the composition. In some embodiments, the polyol may be present in a total amount no more than 12% by weight of the composition. In some embodiments, the polyol may be present in a total amount no more than 10% by weight of the composition. In some embodiments, the polyol may be present in a total amount less than 10% by weight of the composition. In some embodiments, the polyol may be present in a total amount between 5% and 9% by weight.

In some embodiments, the composition may include a plurality of polyols present in a total amount greater than 1% by weight of the composition, and a plurality of polyols present in a total amount less than 0.5% by weight of the composition.

The term "polyol" should be understood as meaning any organic molecule comprising at least two free hydroxyl groups. Preferably, the polyol may be present in liquid form at room temperature.

In various embodiments, the polyol that is suitable for use in the invention may be a compound of linear, branched or cyclic, saturated or unsaturated alkyl type, bearing on each alkyl chain at least two —OH functions, in particular at least three —OH functions and more particularly at least four —OH functions.

In some embodiments, the polyol may contain from 2 to 32 carbon atoms preferably 2 to 20 carbon atoms and more preferably 2 to 16 carbon atoms, advantageously 2 to 10 carbon atoms, more advantageously 2 to 6 carbon atoms.

In some embodiments, the polyol may be a polyethylene glycol.

In some embodiments, the polyol may be a polyhydric alcohol, preferably of C2-C8 and more preferably C3-C6. Non-limiting examples of such include glycerol, pentaerythritol, trimethylolpropane, ethylene glycol, propylene glycol, 1,3-butylene glycol, 1,3-propanediol, pentylene glycol, hexylene glycol, isoprene glycol, dipropylene glycol, diethylene glycol and diglycerol, ethylhexylglycerine, caprylyl glycol and mixtures thereof, glycerol and derivatives thereof, polyglycerols, such as glycerol oligomers, for instance diglycerol, and polyethylene glycols, glycol ethers (especially containing from 3 to 16 carbon atoms) such as mono-, di- or tripropylene glycol (C1-C4)alkyl ethers, mono-, di- or triethylene glycol (C1-C4)alkyl ethers, and mixtures thereof Non-Volatile Silicone Oil.

In some embodiments, the composition may include a non-volatile silicone oil. The term "silicone oil" means an oil containing at least one silicon atom, and in particular containing Si—O groups.

In some embodiments, the composition may include a plurality of non-volatile silicone oil. In some embodiments, the composition may include only two on-volatile silicone oils. In some embodiments, the non-volatile silicone oil may be present in a total amount no more than 20% by weight of the composition. In some embodiments, a first non-volatile silicone oil may be present in a total amount no less than 10% by weight of the composition (such as, e.g., PDMS), and a second non-volatile silicone oil (such as, e.g., an alkyl-dimethicone copolymer) may be present in a total amount no more than 5% by weight of the composition.

In some embodiments, the amount of the hydrocarbon-based oil plus the amount of the non-volatile silicone oil may be less than 30% by weight of the composition. In preferred embodiments, the cosmetic composition may be free of volatile silicone oils.

The non-volatile silicone oils may be non-phenyl silicone oils. The term "non-phenyl silicone oil" denotes a silicone oil not bearing any phenyl substituents. Representative examples of these non-volatile non-phenyl silicone oils which may be mentioned include polydimethylsiloxanes; alkyl dimethicones; vinylmethyl methicones; and also silicones modified with aliphatic groups and/or with functional groups such as hydroxyl, thiol and/or amine groups.

In some embodiments, the alkyl dimethicone may be an alkyl-dimethicone copolymer, such as Lauryl PEG/PPG-18/18 Methicone (which is more particularly an alkoxyl derivative of Lauryl Methicone containing on the average 18 moles of ethylene oxide and 18 moles of propylene oxide, sold under the name "Dow Corning 5200 Formulation Aid" by Dow Corning; cetyl PEG/PPG-10/1 Dimethicone (which is more particularly a copolymer of Cetyl Dimethicone and an alkoxyl derivative of dimethicone containing on the average 10 moles of ethylene oxide and 1 mole of propylene oxide) such as the product sold under the name Abil EM 90 by Evonik Goldschmidt as well as the mixture of cetyl PEG/PPG-10/1 Dimethicone, of polyglycerol isostearate (4 moles) and hexyl laurate sold under the name ABIL WE 09 by Evonik Goldschmidt.

Vitamins.

In some embodiments, the composition may include a vitamin. In some embodiments, the composition may include a plurality of vitamins. Such vitamins include materials having vitamin activity. In some embodiments, the vitamins may be present in a total amount no more than 3% by weight of the composition. In some embodiments, the vitamins may be present in a total amount no more than 2.5% by weight of the composition. In some embodiments, the vitamins may be present in a total amount no less than 0.5% by weight of the composition. In some embodiments, the vitamins may be present in a total amount no less than 1% by weight of the composition. In some embodiments, the vitamins may be present in a total amount of 2%-2.5% by weight of the composition.

Non-limiting examples of such vitamins include Vitamin K, Vitamin B8, Vitamin B12, Thiamine riboflavin, Nicotinamide (also referred to as Niacinamide), Pantothenic acid, Pyridoxine and derivatives, biotin (vitamin B7), folic acid, cyanocobalamin and Ascorbic acid. Vitamins include vitamin derivatives. For example, ascorbic acid (vitamin C) and derivatives thereof, especially the phosphate derivatives thereof such as the potassium salt of di-alpha-tocopheryl diascorbyl phosphate (sold by the company Senju Pharmaceutical under the reference Sepivital EPC), magnesium ascorbyl phosphate and sodium ascorbyl phosphate (sold by the company Roche under the reference Stay-C 50), and esters thereof such as ascorbyl acetate, palmitate and propionate; retinol (vitamin A) and derivatives thereof, especially esters thereof such as retinyl acetate, palmitate and propionate; as well as pantothenic acid (vitamin B) and derivatives thereof such as pantolactone, and D-panthenol.
Preservative.

In some embodiments, the composition may include a preservative. In some embodiments, the composition may include a plurality of preservatives. In some embodiments, the preservative may be present in an amount no more than 1.5% by weight of the composition.

Non-limiting examples of preservatives include phenoxyethanol, benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenesin, Triclosan, Chlorhexidine digluconate, Imidazolidinyl Urea, and Diazolidinyl Urea. Any or all may be used alone or in combination with each other.
Silicone Resin.

The composition according to the invention comprises at least one silicone resin. In some embodiments, the composition only includes a single silicone resin. The term "resin" refers to a compound of which the structure is three-dimensional. As such, in terms of this invention, a polydimethylsiloxane is not a silicone resin.

In some embodiments, the silicone resin may be present in a total amount of no more than 3% by weight of the composition. In some embodiments, the silicone resin may be present in a total amount of no more than 2% by weight of the composition. In some embodiments, the silicone resin may be present in a total amount of 1.5%-2.5% by weight of the composition.

The classification of silicone resins (also called siloxane resins or silicon resins) is known under the name "MDTQ", the resin being described according to the various siloxane monomeric units comprised therein, each of the letters "MDTQ" characterizing a type of unit.

The "letter M" represents the Monofunctional unit having the formula $R1R2R3 \, SiO_{1/2}$, the silicon atom being bound to a single oxygen atom in the polymer comprising this unit.

The letter "D" denotes a Difunctional unit $R1R2SiO_{2/2}$ wherein the silicon atom is bound to two oxygen atoms.

The letter "T" represents a Trifunctional unit having the formula $R1SiO_{3/2}$. Such resins are described for example in "Encyclopedia of Polymer Science and Engineering, vol. 15, John and Wiley and Sons, New York, (1989), p. 265-270, and U.S. Pat. Nos. 2,676,182, 3,627,851, 3,772,247, 5,248, 739 or U.S. Pat. Nos. 5,082,706, 5,319,040, 5,302,685 and 4,935,484.

In the M, D, T patterns defined previously, Ri, namely R1, R2 and R3, identical or different, represent a hydrocarbon radical (in particular alkyl) having from 1 to 10 carbon atoms, a phenyl group, a phenylalkyl group or a hydroxyl group.

Finally, the letter "Q" denotes a Tetrafunctional unit $SiO_{4/2}$ wherein the silicon atom is bound to four oxygen atoms in turn bound to the remainder of the polymer.

Various silicone resins having different properties may be obtained from these various units, the properties of these polymers varying according to the type of monomers (or units), the type and number of the Ri radical or radicals, the polymer chain length, the degree of branching and the pendant chain size.

In some embodiments, the silicone resin may be of the MQ type, of the T type, or of the MQT type.
MQ Resins:

In terms of silicone resins of the MQ type, mention can be made of alkylsiloxysilicates having formula $[(R1)_3SiO_{1/2}]_x$ $(SiO_{4/2})_y$ (MQ units) wherein x and y are integers ranging from 50 to 80, and such that the R1 group is a radical such as defined hereinabove, and preferably is an alkyl group that has from 1 to 8 carbon atoms, or a hydroxyl group, preferably, a methyl group.

One MQ resin may be a trimethylsiloxysilicate. As examples of solid silicone resins of the MQ type of the trimethylsiloxysilicate type, mention can be made of those sold under the reference SR1000 by General Electric, under the reference TMS 803 by Wacker, under the name "KF-7312J" by Shin-Etsu, "DC 749", "DC 593" by Dow Corning.

Like the silicone resins comprising MQ siloxysilicate patterns, mention can also be made of phenylalkylesiloxysilicate resins, such as phenylpropyldimethylsiloxysilicate (Silshine 151 sold by General Electric). The preparation of such resins is described in particular in U.S. Pat. No. 5,817,302.
T Resins:

As examples of silicone resins of the T type, mention can be made of polysilsesquioxanes having formula $(RSiO_{3/2})_x$ (T units) wherein x is greater than 100 and such that the R group is an alkyl group having from 1 to 10 carbon atoms, said polysilsesquioxanes can furthermore include Si—OH terminal groups.

Mention can also be made of polymethylsilsesquioxanes which are polysilsesquioxanes wherein none of the methyl radicals is substituted by another group. Such polymethylsilsesquioxanes are described for example in the document U.S. Pat. No. 5,246,694.

Preferably, polymethylsilsesquioxane resins can be used wherein R is a methyl group, such as for example those sold by Wacker under the reference Resin MK such as Belsil PMS MK: polymer comprising $CH_3 \, SiO_{3/2}$ repetitive units (T units), that may also comprise up to 1% by weight of $(CH_3)_2SiO_{2/2}$ units (D units) and having a mean molecular weight of approximately 10,000 g/mol, or by Shin-Etsu under the references KR-220L consisting of T units having the formula $CH_3SiO_{3/2}$ and having Si—OH (silanol) terminal groups, under the reference KR-242A comprising 98% T units and 2% D dimethyl units and having Si—OH terminal units or under the reference KR-251 comprising 88% T units and 12% D dimethyl units and having Si—OH terminal groups.

MQT Resins:

As a resin comprising MQT patterns, those mentioned in document U.S. Pat. No. 5,110,890 are known. A preferred form of resins of the MQT type are the MQT-propyl resins (also called MQTPr). Such resins that can be used in the compositions according to the invention are in particular those described and prepared in application U.S. Pat. No. 8,124,710, of which the content is incorporated here by reference.

The MQ-T-propyl resin preferably comprises the units: (i) $(R1_3SiO_{1/2})_a$; (ii) $(R2_2SiO_{2/2})_b$; (iii) $(R3SiO_{3/2})_c$; and (iv) $(SiO4/2)_d$, with R1, R2 and R3 independently are a hydrocarbon radical (in particular alkyl) having from 1 to 10 carbon atoms, a phenyl group, a phenylalkyl group or a hydroxyl group and preferably an alkyl radical having from 1 to 8 carbon atoms or a phenyl group, a, b, c and d being molar fractions, a is between 0.05 and 0.5, b is between zero and 0.3, c is greater than zero, d is between 0.05 and 0.6, a+b+c+d=1, with the condition that more than 40% in moles of the R3 groups of the siloxane resinare propyl groups.

Preferably, the siloxane resin comprises the units: (i) $(R1_3SiO_{1/2})_a$; (iii) $(R3SiO_{3/2})_c$; and (iv) $(SiO4/2)_d$, with R1 and R3 independently are an alkyl group having from 1 to 8 carbon atoms, R1 being preferably a methyl group and R3 preferably being a propyl group, a being between 0.05 and 0.5, preferably between 0.15 and 0.4, c being greater than zero, preferably between 0.15 and 0.4, d being between 0.05 and 0.6, preferably between 0.2 and 0.6, or between 0.2 and 0.55, a+c+d=1, and a, c, and d being molar fractions, with the condition that more than 40% in moles of the R3 groups of the siloxane resinare propyl groups.

The siloxane resins can be used according to the invention can be obtained by a method comprising the reaction of: A) an MQ resin comprising at least 80% in moles of units $(R1_3SiO_{1/2})_a$ and $(SiO4/2)_d$, R1 being an alkyl group having from 1 to 8 carbon atoms, an aryl group, a carbinol group or an amino group, a and d being greater than zero, with the a/d ration being between 0.5 and 1.5;

and of

B) a propyl T resin comprising at least 80% in moles of units $(R3SiO_{3/2})_c$, R3 being an alkyl group having from 1 to 8 carbon atoms, an aryl group, a carbinol group or an amino group, c is greater than zero, with the condition that at least 40% in moles of the R3 groups are propyl groups, where the A/B mass ratio is comprised between 95:5 and 15:85, preferably the A/B mass ratio is 30:70.

Advantageously, the A/B mass ration is between 95:5 and 15:85. Preferably, the A/B ratio is less than or equal to 70:30. These preferred ratios have shown to allow for comfortable deposits.

Preferably, the composition according to the invention comprises, as a silicone resin, at least one resin of the MQ type such as described hereinabove.

In preferred embodiments, the silicone resin is a siloxysilicate resin, more preferably a trimethylsiloxysilicate resin.

Thickening Agent.

In some embodiments, the composition may include a thickening agent. In some embodiments, the composition may include a plurality of thickening agents. In some embodiments, the thickening agent is present in an amount less than 3% by weight of the composition. In preferred embodiments, the composition is substantially free of a thickening agent. In more preferred embodiments, the composition is free of a thickening agent.

The thickening agent may be selected from organic and inorganic thickeners. Non-limiting examples of organic thickeners include: (i) associative thickeners; (ii) crosslinked acrylic acid homopolymers; (iii) crosslinked copolymers of (meth)acrylic acid and of (C1-C6)alkyl acrylate; (iv) nonionic homopolymers and copolymers comprising at least one of ethylenically unsaturated ester monomers and ethylenically unsaturated amide monomers; and (v) ammonium acrylate homopolymers and copolymers of ammonium acrylate and of acrylamide. As used herein, the expression "associative thickener" means an amphiphilic thickener comprising both hydrophilic units and hydrophobic units, for example, comprising at least one C8-C30 fatty chain and at least one hydrophilic unit.

pH Adjusting or Buffering Agent.

In some embodiments, the composition may include a pH adjusting and/or buffering agent.

pH adjusters include, but are not limited to, sodium metasilicate, silicate compounds, citric acid, ascorbic acid, and carbonate compounds, and sodium hydroxide.

Non-limiting examples of buffering agents include an acetate buffer (for example, acetic acid+sodium acetate), a phosphate buffer (for example, sodium dihydrogen phosphate+di-sodium hydrogen phosphate), a citrate buffer (for example, citric acid+sodium citrate), a borate buffer (for example, boric acid+sodium borate), a tartrate buffer (for example, tartaric acid×sodium tartrate dihydrate), Tris buffer (for example, tris(hydroxymethyl)aminomethane), or a Hepes buffer (4-(2-hydroxyethyl)-1-piperazineethanesulfonic acid).

In some embodiments, the thickening agent is present in an amount less than 3% by weight of the composition. In some embodiments, the composition is substantially free of both a pH adjuster and buffering agent. In some embodiments, the pH adjuster and buffering agent may be present in a total amount of 0.001-0.5% by weight of the composition.

Electrolyte.

In some embodiments, the composition may include an electrolyte. In some embodiments, the composition may include a plurality of electrolytes. In some embodiments, the composition may only include a single electrolyte. The electrolyte may be present in a total amount no more than 2%, no more than 1.5%, or no more than 1% by weight of the composition. The at least one electrolyte present in the composition can be chosen from, for example, alkali metal salts, for instance sodium chloride, potassium chloride or potassium sulfate.

Flavonoid.

In some embodiments, the composition may include a flavonoid. The flavonoid may be present in a total amount less than 0.1%, less than 0.01%, less than 0.001%, or less than 0.0001% by weight of the composition.

The flavonoid may be a flavanone (derivative of 2,3-dihydro-2-phenylchromen-4-one) such flavanones include: Butin, Eriodictyol, Hesperetin, Hesperidin, Homoeriodictyol, Isosakuranetin, Naringenin, Naringin, Pinocembrin, Poncirin, Sakuranetin, Sakuranetin, and Sterubin. The flavonoid may be a flavanonol (derivative of 3-hydroxy-2,3-dihydro-2-phenylchromen-4-one), such flavanols include: Taxifolin, Aromadedrin, Chrysandroside A, Chrysandroside B, Xeractinol, Astilbin, and Tustin. The flavonoid may be a flavone (derivative of 2-phenylchromen-4-one); such flavones include: Apigenin, Luteolin, Tangeritin, Chrysin, Baicalein, Scutellarein, Wogonin, Synthetic Flavones: Diosmin, and Flavoxate. The flavonoid may be a flavonol (derivative of 3-hydroxy-2-phenylchromen-4-one); such flavonols include: 3-Hydroxyflavone, Azaleatin, Fisetin, Galangin, Gossypetin, Kaempferide, Kaempferol, Isorhamnetin, Morin, Myricetin, Natsudaidain, Pachypodol, Quercetin, Rhamnazin, Rhamnetin, Azalein, Hyperoside, Isoquercitin, Kaempferitrin, Myricitrin, Quercitrin, Robinin, Rutin, Spiraeoside, Xanthorhamnin, Amurensin, Icariin, and Troxerutin.

Synthetic Peptide.

In some embodiments, the composition may include a synthetic peptide. The synthetic peptide may be present in a total amount less than 0.1%, less than 0.01%, less than 0.001%, or less than 0.0001% by weight of the composition. In some embodiments, such synthetic peptides include iamin, the biopeptide CL, or various palmitoyl peptides, such as palmitoyl tripeptide-1 or palmitoyl tetrapeptide-7.

Amino Acid or Amino Acid Derivative.

In some embodiments, the composition may include an amino acid or amino acid derivative. In some embodiments, the composition may include an amino acid or amino acid derivative. The amino acid or amino acid derivative may be present in a total amount less than 0.5%, or less than 0.1% by weight of the composition.

For example, one amino acid that may be used is adenosine. Examples of adenosine derivatives that may in particular be mentioned are non-phosphated adenosine derivatives such as: 2'-deoxyadenosine; 2',3'-isopropoylidene adenosine; toyocamycin; 1-methyladenosine; N-6-methyladenosine; adenosine N-oxide; 6-methylmercaptopurine riboside; or 6-chloropurine riboside. Other adenosine derivatives comprise agonists of adenosine receptors including phenylisopropyl-adenosine ("PIA"), 1-methylisoguanosine, N6-cyclohexyladenosine (CHA), N6-cyclopentyladenosine (CPA), 2-chloro-N-6-cyclopentyladenosine, 2-chloroadenosine, N6-phenyladenosine, 2-phenylaminoadenosine, MECA, N6-phenethyladenosine, 2-p-(2-carboxy-ethyl) phenethyl-amino-5'-N-ethylcarboxamido-adenosine (CGS-21680), N-ethylcarboxamido-adenosine (NECA), 5' (N-cyclopropyl)-carboxamidoadenosine, DPMA (PD 129,944) and metrifudil. Other adenosine derivatives include compounds that increase the intracellular concentration of adenosine, such as erythro-9-(2-hydroxy-3-nonyl) adenine ("EHNA") or iodotubercidine. Still more adenosine derivatives include salts and alkyl esters.

In some embodiments, the composition may include the mattifying filler, colorant, hydrocarbon-based oil, hydrocarbon-based emulsifier, water, and UV filter system, may optionally include a polyol, a non-volatile silicone oil, a vitamin, a preservative, a silicone resin, a thickening agent, a pH adjusting or buffering agent, an electrolyte, a flavonoid, a synthetic peptide, and/or an amino acid or amino acid derivative, may be free of a volatile silicone oil, and may be substantially free of all other materials.

Antioxidant.

In some embodiments, the composition may include an antioxidant. In some embodiments, the composition may include a plurality of antioxidants. In some embodiments, the composition may include only a single antioxidant. The antioxidant may be present in a total amount less than 0.5%, or less than 0.2% by weight of the composition.

Non-limiting examples of antioxidants include polyphenols, tannic acid, epigallocatechins and the natural extracts containing them, anthocyanins, pentaerythrityl tetra-di-t-butyl hydroxyhydrocinnamate, rosemary extracts, lens esculenta (lentil) seed extract, olive leaf extracts, green tea, resveratrol and its compounds, pycnogenol, ergothineine, N-acetylcysteine, idebenone, plant extracts such as PRONALEN BIOPROTECT™ from Provital, co-enzyme Q10, bioflavonoids, SOD, phytantriol, lignans, melatonin, pidolates and gluthatione.

Active Materials.

In some embodiments, the composition may include certain active materials. In some embodiments, the composition may include a plurality of active materials. In some embodiments, the composition may include only a single active material. The active material may be present in a total amount less than 0.5%, or less than 0.25% by weight of the composition.

In some embodiments, the active material may include a derivative of hyaluronic acid, such as sodium hyaluronate. In some embodiments, the derivative of hyaluronic acid may be present in a total amount less than 0.2% by weight of the composition. In some embodiments, the derivative of hyaluronic acid may be present in a total amount no more than 0.1% by weight of the composition. In some embodiments, the derivative of hyaluronic acid may be present in a total amount of 0.05-0.15% by weight of the composition.

In some embodiments, the active material may include a chelating agent. In some embodiments, the composition may include a plurality of chelating agents. In some embodiments, the composition may include only a single chelating agent. In some embodiments, the chelating agent may be present in a total amount less than 0.2% by weight of the composition. In some embodiments, the chelating agent may be present in a total amount of 0.05-0.15% by weight of the composition.

Non-limiting examples of a chelating agent include aminocarboxylic acids (i.e. acids comprising at least one carboxylic acid group) such as the compounds having the following INCI name: phytic acid, diethylenetriaminepentaacetic acid (DTPA), ethylenediaminedisuccinic acid (EDDS) and trisodium ethylenediamine disuccinate such as Octaquest E30 from Octel, ethylenediaminetetraacetic acid (EDTA), ethylenediamine-N,N'-diglutaric acid (EDDG), glycinamide-N,N'-disuccinic acid (GADS), 2-hydroxypropylenediamine-N,N'-disuccinic acid (HPDDS), ethylenediamine-N,N'-bis(ortho-hydroxyphenylacetic acid) (EDDHA), N,N'-bis(2-hydroxybenzyl)ethylenediamine-N,N'-diacetic acid (HBED), nitrilotriacetic acid (NTA), methylglycine diacetic acid (MGDA), N-2-hydroxyethyl-N, N-diacetic acid and glyceryl imino diacetic acid (as described in documents EP-A-317 542 and EP-A-399 133), iminodiacetic acid-N-2-hydroxypropyl sulfonic acid and aspartic acid N-carboxymethyl N-2-hydroxypropyl-3-sulfonic acid (as described in EP-A-516 102), beta-alanine-N,N'-diacetic acid, aspartic acid-N,N'-diacetic acid and aspartic acid-N-monoacetic acid (described in EP-A-509 382), chelating agents based on iminodisuccinic acid (IDSA) (as described in EP-A-509 382), ethanoldiglycine acid, phosphonobutane tricarboxylic acid, such as the compound sold by Bayer under the reference Bayhibit AM, tetrasodium glutamate diacetate (GLDA) such as Dissolvine GL38 or 45S from Akzo Nobel, chelating agents based on mono- or polyphosphonic acid, such as the compounds having the following INCI name: diethylenetriaminepenta (methylenephosphonic acid) (DTPMP), ethane-1-hydroxy-1,1,2-triphosphonic acid (E1HTP), ethane-2-hydroxy-1,1,2-triphosphonic acid (E2HTP), ethane-1-hydroxy-1,1-diphosphonic acid (EHDP), ethane-1,1,2-triphosphonic acid (ETP), ethylenediaminetetramethylenephosphonic acid (EDTMP), hydroxyethane-1,1-diphosphonic acid (HEDP), chelating agents based on polyphosphoric acid, such as the compounds having the following INCI name: sodium tripolyphosphate (STP), tetrasodium diphosphate, hexametaphosphoric acid, sodium metaphosphate, phytic acid, salts and derivatives thereof, and mixtures thereof.

In some embodiments, the active material may be an active ester or derivative thereof. The active ester or derivative may be present in a total amount less than 0.1%, less than 0.01%, less than 0.001%, or less than 0.0001% by weight of the composition. Active esters are well known in peptide synthesis and refer to certain esters that are easily reacted with an amine of an amino acid under conditions commonly used in peptide synthesis. One common at-live ester is N-Hydroxysuccinimide, and a commonly used form of that active ester is the N-hydroxysuccinimidyl (NHS) ester.

In some embodiments, the composition may include the mattifying filler, colorant, hydrocarbon-based oil, hydrocarbon-based emulsifier, water, and UV filter system, may optionally include a polyol, a non-volatile silicone oil, a vitamin, a preservative, a silicone resin, a thickening agent, a pH adjusting or buffering agent, and an electrolyte, may be free of a volatile silicone oil, and may be substantially free of all other materials.

In some embodiments, the composition may include the mattifying filler, colorant, hydrocarbon-based oil, hydrocarbon-based emulsifier, water, and UV filter system, may optionally include a polyol, a non-volatile silicone oil, a vitamin, a preservative, a silicone resin, a thickening agent, a pH adjusting or buffering agent, an electrolyte, a flavonoid, a synthetic peptide, an antioxidant, an active material, and/or an amino acid or amino acid derivative, may be free of a volatile silicone oil, and may be substantially free of all other materials.

Example

An inventive example such as that shown in Table 1, below, can be created by first mixing the oils, oil-soluble ingredients and the inorganic UV filter in a container, then mixing the water and water-soluble ingredients in a separate container, then while homogenizing, combining the two phases, and then adding the mattifying fillers and colorants.

TABLE 1

| Material | % by Weight (Active Basis) |
| --- | --- |
| Silica Aerogel | 0.5-1% |
| Amorphous Silica | 3-5% |
| Modified Starch | 1-2% |
| Clay (Kaolin) | <0.01% |
| Silicone Elastomer | 1-2% |
| Octyl Salicylate | 4-5% |
| Phenylbenzimidazole sulfonic acid | 3-4% |
| UV-grade Titanium Dioxide | 2-3% |
| Coated Iron Oxide Pigments | 1-2% |
| Pigment-grade titanium dioxide | 15-20% |
| Pearlescent Pigment | 1-3% |
| Hydrocarbon-Based Oils (C8-C16 Alkanes) | 6-10% |
| Hydrocarbon-Based Oils (Other Synthetic Esters) | 2-4% |
| Hydrocarbon-Based Emulsifier | 1.5-2.5% |
| Water | 15-20% |
| Polyols | 5-9% |
| Non-volatile silicone oil (dimethicone) | 15-20% |
| Non-volatile silicone oil (alkyl-dimethicone copolymer) | 3-5% |
| Vitamins | 1-3% |

TABLE 1-continued

| Material | % by Weight (Active Basis) |
| --- | --- |
| Preservatives | 0.5-1.5% |
| MQ resin | 1-2% |
| pH adjusting or buffering agent | 0.1-0.5% |
| Electrolyte | 0.5-1% |
| Active Material | 0.1-0.3% |
| Antioxidant | 0.1-0.3% |
| Amino acid or amino acid derivative | 0.0001-0.1% |
| Flavonoid | <0.0001% |
| Synthetic Peptide | <0.0001% |

The above formulas can provide all day matte finish and shine control, as well an optical blurring effect to minimize the appearance of pores and skin texture. Over time, the above formulas also improve dryness, skin tone and texture, pore appearance, appearance of blemishes, and visible signs of aging. The SPF provided will vary based on the levels of UV filters actually used, but as will be understood by those of skill in the art, SPF values will increase as the amount of UV filters used increases. For example, some of the formula described in Table 1 can provide SPF values >40.

In some embodiments, a method may be provided for applying cosmetics to a face. The method may include applying the cosmetic composition as disclosed herein to the face during a first period of time, and then removing the cosmetic composition from the face during a second period of time after the first period of time. In some embodiments, the method may include applying a second composition over the cosmetic composition after the first period of time and before the second period of time.

What is claimed is:

1. A cosmetic composition for providing a matte foundation, comprising:
 a mattifying filler consisting of a silica aerogel and optionally a modified starch, amorphous silica, a clay, and/or a silicone elastomer, where the mattifying filler is present in an amount greater than 0% and less than 10% by weight of the cosmetic composition;
 an organic hydrophobic ultraviolet filter consisting of octyl salicylate, the cosmetic composition being free of other organic hydrophobic ultraviolet filters;
 an organic water-soluble ultraviolet filter consisting of 2-phenylbenzimidazole-5-sulfonic acid (PBSA), the cosmetic composition being free of other organic water-soluble ultraviolet filters;
 an inorganic ultraviolet filter consisting of ultraviolet (UV)-grade titanium dioxide in an amount greater than 0% and less than 5% by weight of the cosmetic composition, the cosmetic composition being free of other inorganic ultraviolet filters;
 a colorant consisting of one or more pigments, where the colorant is present in an amount greater than 0% to less than 30% by weight of the cosmetic composition, where each pigment is coated, and where the one or more pigments comprises pigment-grade titanium dioxide;
 a polyol;
 a vitamin;
 a non-volatile silicone oil;
 a hydrocarbon-based oil, where the hydrocarbon-based oil is present in an amount greater than 0% and less than 15% by weight of the cosmetic composition, and where the amount of the hydrocarbon-based oil plus the amount of the non-volatile silicone oil is greater than 0% and less than 30% by weight of the cosmetic composition;

a hydrocarbon-based emulsifier;

water;

wherein the cosmetic composition is free of volatile silicone oils;

wherein the cosmetic composition includes at least one additional material, the at least one additional material being a preservative, a silicone resin, a thickening agent, a pH adjusting or buffering agent, an electrolyte, a flavonoid, a synthetic peptide, and/or an amino acid or amino acid derivative; and wherein the cosmetic composition is substantially free of all other materials.

2. The cosmetic composition according to claim 1, wherein the inorganic ultraviolet filter is present in an amount greater than 0% and less than 3% by weight of the cosmetic composition.

3. The cosmetic composition according to claim 1, wherein the cosmetic composition is a water-in-oil emulsion.

4. A method for applying cosmetics to a face, comprising:

applying the cosmetic composition according to claim 1 to the face during a first period of time; and removing the cosmetic composition from the face during a second period of time after the first period of time.

5. The method according to claim 4, further comprising applying a second composition over the cosmetic composition after the first period of time and before the second period of time.

* * * * *